(12) United States Patent
Pang et al.

(10) Patent No.: US 8,802,630 B2
(45) Date of Patent: Aug. 12, 2014

(54) METHOD OF TREATING BRAIN INJURY

(71) Applicant: Buddhist Tzu Chi General Hospital, Hualien (TW)

(72) Inventors: Cheng-Yoong Pang, Hualien (TW); Mei-Jen Wang, Hualien (TW); Hock Kean Liew, Hualien (TW); Hsin-Yi Huang, Hualien (TW); Chih-Wei Hsu, Hualien (TW); Jon-Son Kou, Hualien (TW); Ting-Yi Li, Hualien (TW); Hsiao-Fen Peng, Hualien (TW); Jia-Yi Wang, Hualien (TW)

(73) Assignee: Buddhist Tzu Chi Medical Foundation, Hualien (TW)

( * ) Notice: Subject to any disclaimer, the term of this patent is extended or adjusted under 35 U.S.C. 154(b) by 0 days.

(21) Appl. No.: 13/670,707

(22) Filed: Nov. 7, 2012

(65) Prior Publication Data

US 2013/0123177 A1    May 16, 2013

Related U.S. Application Data

(60) Provisional application No. 61/557,042, filed on Nov. 8, 2011.

(51) Int. Cl.
*A01N 37/18*    (2006.01)
*A61K 38/00*    (2006.01)
*C07K 14/00*    (2006.01)

(52) U.S. Cl.
USPC .................. 514/17.7; 514/21.2; 530/350

(58) Field of Classification Search
None
See application file for complete search history.

(56) References Cited

PUBLICATIONS

Pan et al., Progress in Neurobiology, 2008, 84:148-56.*
Abuirmeileh et al., J. Neuroinflammation, 2007, 4:19, pp. 1-5.*
Wang et al., J. Immunology, 2007, 179:6204-14.*
Huang et al., Neurobiology of Aging, 2011, 32:1662-7.*
Facci et al., Neuropharmacology, 2003, 45:623-36.*
Roe et al., Eur. J. Neuroscience, 1998, 10:553-9.*
Liew et al., "Urocortin Reduces Intracerebral Hemorrhage-Induced Injury in Rats", The 4th AFLAS Congress Meeting (Nov. 9-11, 2010).

* cited by examiner

*Primary Examiner* — Olga N Chernyshev
(74) *Attorney, Agent, or Firm* — Edwards Wildman Palmer LLP; Peter F. Corless; Richard B. Emmons

(57) ABSTRACT

A novel use of a neuropeptide for treating brain injury in a subject in need thereof is provided. The present invention also provides various amenable routes of administering urocortin, that is, via injection intracerebroventricularly and intraperitoneally, and via intravenous bolus administration.

14 Claims, 13 Drawing Sheets

METHOD OF TREATING BRAIN INJURY

CROSS-REFERENCE TO RELATED APPLICATIONS

This application claims the benefit of U.S. Provisional Application No. 61/557,042, filed on Nov. 8, 2011, the entire contents of which is incorporated herein by reference.

BACKGROUND OF THE INVENTION

1. Field of the Invention

The present invention relates to a method for treating brain injury in a subject. The present invention relates particularly a method of using a neuropeptide to treat brain injury in a subject.

2. Description of Related Art

Spontaneous intracerebral hemorrhage (ICH) accounts for approximately 15% of stroke incidents in Western populations, and may even be higher (up to 20 to 30%) in Asian populations (Qureshi et al., 2001). Being one of the most lethal forms and destructive type of stroke, mortality of ICH is high at 30% to 50% (Rosamond et al., 2008). The prognosis of patients with ICH is poor.

Despite a number of promising trials, no medical or surgical therapy has been convincingly shown to benefit ICH patients (Hanggi and Steiger, 2008). No drug can convincingly benefit patients and effectively increase survival in ICH patients (Pouratian et al., 2003). The early surgical removal of the blood clot has shown no overall benefits when compared with conventional therapies (Hankey and Hon, 1997; Mendelow et al., 2005; Morgenstern et al., 2001).

Pathological changes of ICH can be divided into primary and secondary brain injury. Primary injury occurs rapidly as a result of physical destruction of tissues, and mass effect of the hematoma leading to increased intracranial pressure (Qureshi et al., 2001). Secondary injury commonly occurs when tissue reacts to the invasion of the blood breakdown components in the parenchyma adjacent to hematoma, initiating the activation of inflammatory cells, brain edema, blood-brain bather (BBB) disruption and apoptosis. Secondary injury often takes hours to days after ICH insult (Wang, 2010), making it a practical therapeutic target.

Urocortin, a 40-amino-acid endogenous neuropeptide, belongs to the corticotrophin releasing hormone (CRH) family, sharing two G-protein coupled receptors, CRH-R1 and CRH-R2 (Fekete and Zorilla, 2007; Hsu and Hsueh, 2001). Urocortin is expressed in brain neurons and glial cells (Pedersen et al., 2002; Perrin and Vale, 1999; Stevens et al., 2003; Van Pett et al., 2000), in a variety of brain regions including the supraoptic nucleus, Edinger-Westphal nucleus and the sphenoid nucleus (Pan and Kastin, 2008).

Besides being involved in the regulation of anxiety, learning and memory, body temperature, stress responses (Pan and Kastin, 2008) and hypotension (Fekete and Zorilla, 2007; Torpy et al., 1999), urocortin is also a powerful anti-inflammatory agent and a potential therapeutic drug for heart ischemia/reperfusion injury (Brar et al., 2000; Gordon et al., 2003; Lawrence et al., 2002; and Liu et al., 2005).

As such, in view of the limitations of current management therapies on ICH-induced brain injuries, additional strategies to combat ICH-induced brain injuries need to be provided. The present invention provides such strategies that can effectively reduce the incidence of ICH-induced brain injury.

SUMMARY OF THE INVENTION

In one embodiment, a method for treating brain injury in a subject is provided. The method comprises administering an effective amount of a neuropeptide to the subject in need thereof, wherein the brain injury comprises one or more of neuronal cytotoxicity, neuronal loss, brain edema, blood brain barrier damage, or sensory-motor behavioral deficit, and wherein the brain injury is caused by one or more of an attack, intracerebral hemorrhage, asphyxia, drowning, brain infection, brain poisoning, brain ischemia, brain hypoxia, brain contusion, or brain concussion.

In one embodiment, the neuropeptide is administered to the subject by one of intracerebroventricular injection, intraperitoneal injection, intravenous bolus administration, or any combination thereof. In one embodiment, the neuropeptide is delivered intracerebroventricularly to the subject at an amount of about 0.05 to about 5 µg/kg per subject, delivered intraperitoneally to the subject at an amount of about 0.5 to about 25 µg/kg per subject, and delivered intravenously to the subject in the form of a bolus at an amount of about 2.5 to about 25 µg/kg per subject. In another embodiment, the neuropeptide is delivered intraperitoneally to the subject at an amount of about 1 to about 4 µg/kg per subject.

In one embodiment, the neuropeptide is urocortin. In another embodiment, the neuropeptide is one of naturally occurring human urocortin, naturally occurring non-human urocortin, or non-naturally occurring urocortin, wherein the non-naturally occurring urocortin is one of recombinantly produced urocortin, a fragment of urocortin, an analog of urocortin or a derivative of urocortin.

In one embodiment, the treatment of brain injury is to reduce brain injury, wherein the reduction of brain injury comprises suppression one or more of microglial activation, inflammatory cytokine production, brain edema, or blood-brain bather damage.

In one embodiment, the subject is a mammal In another embodiment, the subject is human.

In one embodiment, the effective amount of urocortin administered to the subject is efficacious to the subject with hypertension.

DETAILED DESCRIPTION OF THE EMBODIMENTS

Figure 1:
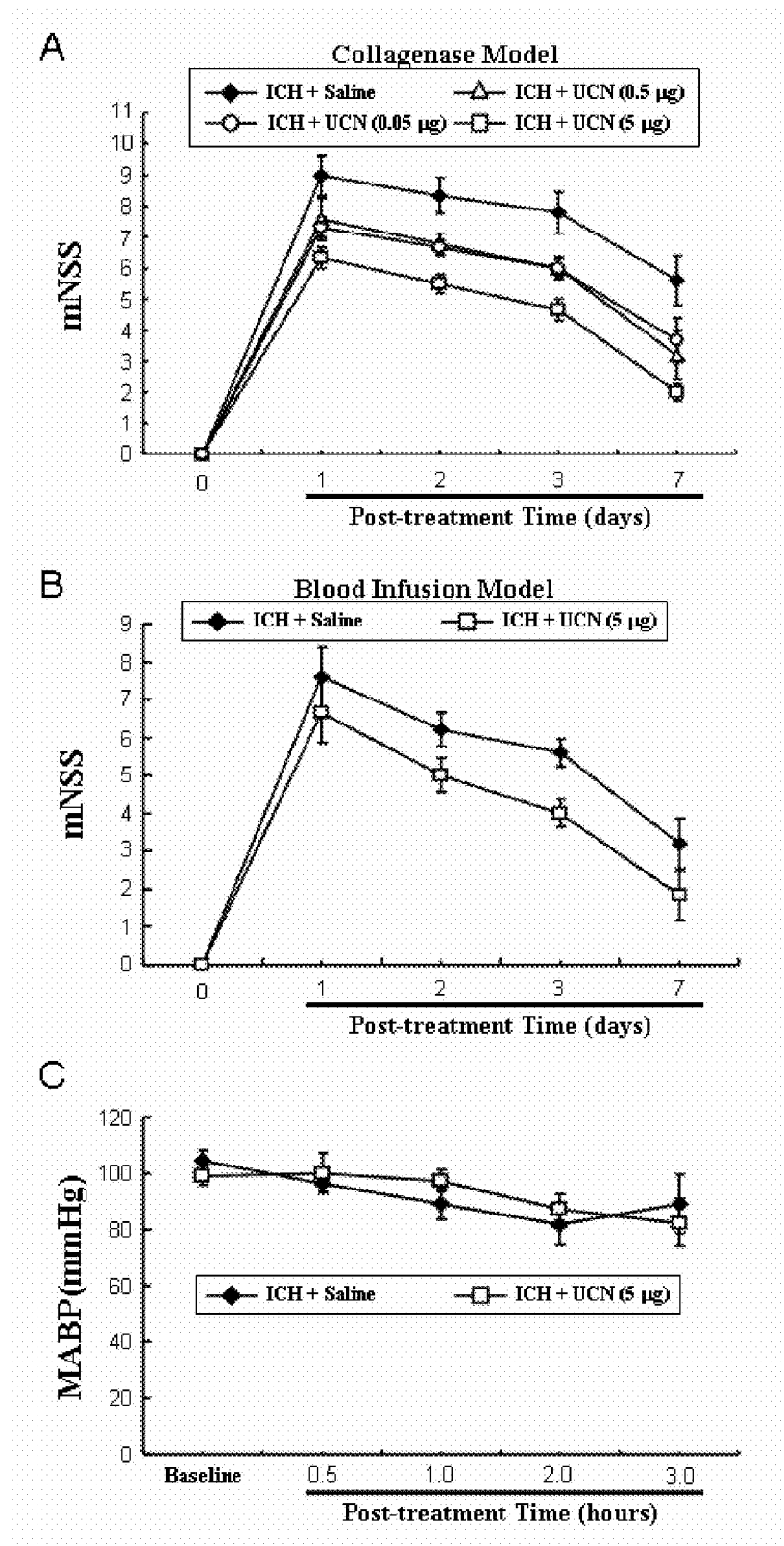
FIG. 1 shows dose-dependent effects of intracerebroventricular administration of UCN on mNSS of ICH rats. (A) Collagenase-induced ICH rats were injected with saline (vehicle) or UCN (0.05, 0.5, and 5 µg) intracerebroventricular injection at one hour after the ICH. The mNSS was measured on 1, 2, 3, and 7 days after ICH insult. $P<0.001$ versus saline group (by Tukey post hoc test following repeated measure ANOVA) (n=6). (B) Autologous blood infusion-induced ICH rats were injected with saline or UCN (5 µg, i.c.v.). Data represent means±SEM. $P<0.05$ versus saline group (by two-way ANOVA) (n=6). The mNSS of all rats before the ICH was 0 on the 0 day. The higher the mNSS scores, the severer the deficit. (C) Changes in mean arterial blood pressure over 3 hours after UCN administration (5 µg i.c.v.) (n=4).

Various specific details are provided herein to provide a more thorough understanding of the invention.

Models for the Intra-cerebral Hemorrhage (ICH): Blood Infusion Model and Collagenase Induction Model The ICH refers to hemorrhage in the striatum, a part of the brain. Male Sprague-Dawley rats (250-300 g) anesthetized with chloral hydrate (0.4 g kg$^{-1}$ i.p., Sigma-Aldrich, St. Louis, Mo., USA). The blood infusion model of ICH was induced by intrastriatal (0.0 mm posterior, 3.0 mm right, 5.0 mm ventral to bregma skull surface) infusion of autologous blood (100 μl within 1 minute) and stereotaxic administration of bacterial collagenase VII-S into the striatum (MacLellan et al. 2008; Rosenberg et al. 1990). Briefly, bacterial collagenase VII-S (0.23 U in 1.0 μl sterile saline, Sigma-Aldrich) was infused into the striatum over a period of 10 minutes. The needle was kept in place for another 10 minutes to prevent backflow. The craniotomies were sealed with bone wax. The rats were allowed to recover in separate cages at room temperature.

Experimental Design

All experimental protocols were approved by the Animal Care and Use Committee of the Buddhist Tzu Chi University, Taiwan in accordance with guidelines set by the National Institutes of Health Guide for the Care and Use of Laboratory Animals Animals were housed under a 12 hours light/dark cycle with free access to food and water. Utmost efforts were made to minimize the suffering and the number of animals used.

In intracerebroventricular experiments, totally 97 rats were randomly divided into the following five groups:

1. Sham ICH control group, n=4. Rats were infused with 1 μl saline (0.1 μl/minute for 10 minutes) into the striatum.

2. ICH+Saline group, collagenase model, n=39. One hour after infusion with the collagenase (induction of the ICH), rats received an infusion of saline (0.5 μl/minute for 10 minutes) into the lateral ventricle (1.0 mm posterior, 1.4 mm right, 3.4 mm ventral to bregma of dura surface) ipsilateral to the ICH striatum.

3. ICH+UCN group, collagenase model, n=46. One hour after the induction of ICH, UCN (0.05, 0.5 and 5 μg in 5 μl saline) was infused (0.5 μl/minute for 10 minutes) into the lateral ventricle same as group 2.

4. ICH+Saline group, blood infusion model, n=6. One hour after the induction of ICH by autologous blood (100 μl) infused into the striatum, rats received an infusion of saline (0.5 μl/minute for 10 minutes) into the lateral ventricle, ipsilateral to the ICH striatum.

5. ICH+UCN group, blood infusion model, n=6. One hour after the induction of ICH by autologous blood infusion same as group 4, UCN (5 μg in 5 μl saline) was infused (0.5 μl/minute for 10 minutes) into the lateral ventricle.

The dosages of UCN in intracerebroventricular routes were obtained from empirical trials, because there is no available investigation on the therapeutic dosage of UCN for ICH treatment.

In intraperitoneal experiments, totally 149 rats were randomly divided into the following four groups:

1. Sham +Saline group (n=17). Rats were infused with 1 μl saline (over a period of 10 min) into the striatum to mimic the collagenase infusion. At 60 minutes post sham ICH induction, a total of 0.2 ml of sterile saline was administrated intraperitoneally to control for urocortin (UCN) treatment in the treatment group.

2. ICH+Saline group, collagenase model (n=42). A total 0.2 ml of sterile saline was administrated intraperitoneally to each animal at 60 minutes post-ICH induction.

3. ICH+L-UCN, collagenase model (n=42) group. Low dose (2.5 μg/kg in 0.2 ml sterile saline, intraperitoneally) of UCN was administrated to each animal at 60 minutes post-ICH.

4. ICH+H-UCN, collagenase model (n=20) group. High dose (25 μg/kg in 0.2 ml sterile saline, intraperitoneally) of UCN was administrated to each animal at 60 minutes post-ICH.

5. ICH+Saline group, blood infusion model, n=6. One hour after the induction of ICH by autologous blood (100 μl) infused into the striatum, rats received an injection of saline (0.2 ml, intraperitoneally).

6. ICH+UCN group, blood infusion model, n=6. One hour after the induction of ICH by autologous blood infusion same as group 5, UCN (2.5 μg/kg in 0.2 ml sterile saline, intraperitoneally) was administrated to each animal at 60 minutes post-ICH.

The UCN dosage range in intraperitoneal route was chosen for dose-dependent therapeutic effect according to the previous studies in myocardial infarction and cardiovascular function (Torpy et al., 1999; Maillot et al., 2003; Wang et al., 2001).

Assessment of Neurological Abnormalities

Rats were used in the assessment of the neurological abnormalities with a modified Neurological Severity Score (mNSS) method (Chen et al. 2001) by an investigator blinded to the experimental treatment scheme. The mNSS is a composite test of motor, sensory, and balance functions. The assessment was performed before and on 1, 3 and 7 days after the ICH. Neurological functions were graded on a scale of 0-18 (normal score, 0; maximal deficit score, 18).

Evaluation of Physiological Parameters

Rats were randomly assigned for evaluation of physiological parameters including mean arterial blood pressure, blood gases, body weight changes and body temperature. Under urethane (urethane (1.0 g/kg bodyweight, intraperitoneally, Sigma-Aldrich) anesthesia, a femoral artery was cannulated with a PE-50 polyethylene tube for fluid supplementation and monitoring of arterial blood pressure and blood gas. Arterial blood pressure was recorded through an amplifier (MP35, BIOPAC system, Inc.) and stored in a PC computer. Body temperature (rectal temperature) was automatically maintained at 37.5±0.5° C. by a rectal temperature sensor and a heating pad (CMA-150, Sweden). The physiological parameters were measured before (baseline) and after treatment (UCN or Saline) 0.5, 1 and 3 hours.

Assessment of Brain Edema

Brain edema formation peaks on day 3 post-ICH (Xue et al., 2000; Yang et al., 1994). This time point, hence, was chosen for studying brain edema as indicated by tissue water content. Rats were randomly used in the assessment of brain water content by using a common wet/dry method as previously described (Chu et al., 2004). Briefly, 3 days post-ICH, rats were anesthetized and decapitated. The brains were removed and separated into contralateral, ipsilateral hemispheres and cerebellum. The cerebellum was used as an internal control. Sample was weighed to obtain the wet weight immediately, and then dried in an oven at 100° C. for 24 hours to obtain the dry weight. The water content was expressed as a percentage of the wet weight: [(wet weight)−(dry weight)] (wet weight)$^{-1}$×100%.

Evaluation of UCN Penetration into the Brain

The UCN was labeled with the Alexa Fluor® 488 using Microscale Protein Labeling Kit (A30006, Invitrogen, USA), according to manufacturer's instruction. The Alexa Fluor® 488 dye-labeled UCN (2.5 μg) with the fluorescence excitation and emission maxima of approximately 494 and 519 nm was administered intraperitoneally one hour after ICH. Three hours after the fluorescence-labeled UCN injection, the rats were re-anesthetized with chloral hydrate (0.4 g/kg) intraperitoneally, and their brains were removed immediately without perfusion, and sectioned into 20 μm thickness by a cryostat. After nuclei counter-stained with DAPI, the slides were washed and mounted on cover slips with anti-fading mounting medium (VECTASHIELD®, USA). The penetration of the labeled UCN into the striatum was evaluated under fluorescence microscope.

Assessment of Hemorrhagic Volume

Rats were randomly used in assessment of hemorrhagic volume at 24 hours (day 1) post-ICH. The accumulated hemorrhagic volume was quantified by a spectrophotometric assay as reported by Park et al., with minor modification (Park et al., 2005). Briefly, both contralateral and ipsilateral hemispheres were obtained after transcardial perfusion. PBS was added to the individual hemispheres to make-up a total of 3 ml volume for homogenization and centrifugation (15000 g, 30 minutes). The supernatant (40 μl) was reacted with Drabkin's reagent (160 μl, Sigma) for 15 minutes at room temperature. Optical density was measured at 540 nm with a spectrophotometer (Molecular Devices OptiMax, USA). Equivalent hemorrhage volume (μl) of the supernatant was calculated from a standard curve obtained with known amounts of the blood.

Morphometric Measurement of Lesion Volume

Rats' brain images were collected from the brain edema and cytokine ELISA assay groups on day 3 post-ICH. The brains were cut coronally through the needle entry site (identifiable on the brain surface), and then serially sliced (2-mm thickness) anteriorly and posteriorly to the needle entry site. Digital photographs of the serial slices were taken and lesion volume was computed using image analyzer program (Image J, NIH). The total lesion volume (mm$^3$) was computed by summing the residual blood clot and damaged area in each section and multiplying by the distance between sections (Jung et al., 2004).

Assessment of Blood-Brain Barrier (BBB) Disruption

Rats were randomly used in assessment of the vascular permeability of BBB with a modified Evans blue extravasation method (Esen et al., 2005). Briefly, 70 hours post-ICH, rats were anesthetized with chloral hydrate (0.4 g/kg) and infused, via the right femoral vein with 37° C. Evans blue dyes (2% in 0.9% normal saline, 4 ml/kg) over 5 minutes. Two hours later, the rats were perfused with 300 ml normal saline to wash out any remaining dye in the blood vessels and then brains were removed and sectioned into 2 mm thickness by a rodent brain matrix. Coronal brain sections were taken starting at +2 mm and ending at −4 mm from Bregma. BBB permeability was evaluated in the striatum, cortex and cerebellum. The cerebellum was used as an internal control. Each portion was weighed immediately and placed in 1 ml of 0.9% normal saline for homogenization of the sample. For protein precipitation, 1 ml of 60% trichloroacetic acid solution was added and vortexed for 2 minutes. The mixture was subsequently cooled for 30 minutes and centrifuged (1500 g at 4° C.) for another 30 minutes. The absorbance of Evans blue in the supernatant was then measured with a spectrophotometer (Molecular Devices OptiMax, USA) at 610 nm The dye concentration was expressed as μg/g of tissue weight and calculated from a standard curve obtained from known amounts of the dye.

Assessment of Cytokines

Rats were used for the cytokine assay by ELISA. The ipsilateral striatal tissues were collected before and on days 1, 3 and 7 days post-ICH. After homogenization in the lysis buffer (PRO-PREP™, iNtRON Biotechnology, Korea) and centrifuged at 12,000 g for 30 minutes, the supernatants were collected and stored frozen at −80° C. During quantification, the cytokines (TNFα, IL-1β and IL-6) were normalized to 100 μg of proteins in the supernatant using a commercial ELISA kit from R & D Systems (Minneapolis, Minn., USA) according to the manufacturer's instructions.

Immunohistochemistry

Rats were used in immunohistochemistry on day 3 post-ICH. Rats were anesthetized as described above and transcardially perfused with cold 0.1 M phosphate buffer saline followed by cold 4% paraformaldehyde in 0.1 M phosphate-buffered saline. Brains were removed and immersed in 4% paraformaldehyde for 24 hours and 30% sucrose for another 24 hours. Coronal brain sections (20 μm thickness) were cut and collected from 0.0 to −2.0 mm AP to bregma using a cryostat (Leica CM 1900). Three 20 μm coronal sections, representing the core of the hematoma, were taken starting at 0.0 mm from bregma (the needle entry site). Additional adjacent serial coronal sections taken through the center of the hemorrhagic lesion were processed for the counting of marker-specific cells (Jung et al., 2004). Antibodies of OX-42 (1:100; BD, USA), ED-1 (1:100; BD, USA) were used as microglial markers, and NeuN (1:200, Chemicon, USA) was used as neuron marker. Tissues sections were incubated with the primary antibodies overnight at 4° C. The bound primary antibody was visualized by incubation with an appropriate biotinylated secondary antibody followed by the Vectastain ABC reagents and color development with 3,3'-diaminobenzidine. Negative control slices from each animal were prepared for immunohistochemical staining processed in an identical manner except the primary antibodies were added. The numbers of positive cells in the same focal plane were counted in 6 regions of interest around the ipsilateral striatum (perihematomal region, 1 mm$^2$) All cell counting was done by an independent investigator counted the positive cells.

Statistical Analysis

Data were analyzed statistically using the software Prism for Student's t-test and are presented as mean±standard errors of the mean (SEM). The statistical comparisons among multiple groups were made using one-way ANOVA followed by Bonferroni correction. In all instances, n refers to the number of animals in a particular group. P value of <0.05 is considered statistically significant.

EXAMPLES

UCN Reduces Neurological Deficits

Figure 2:
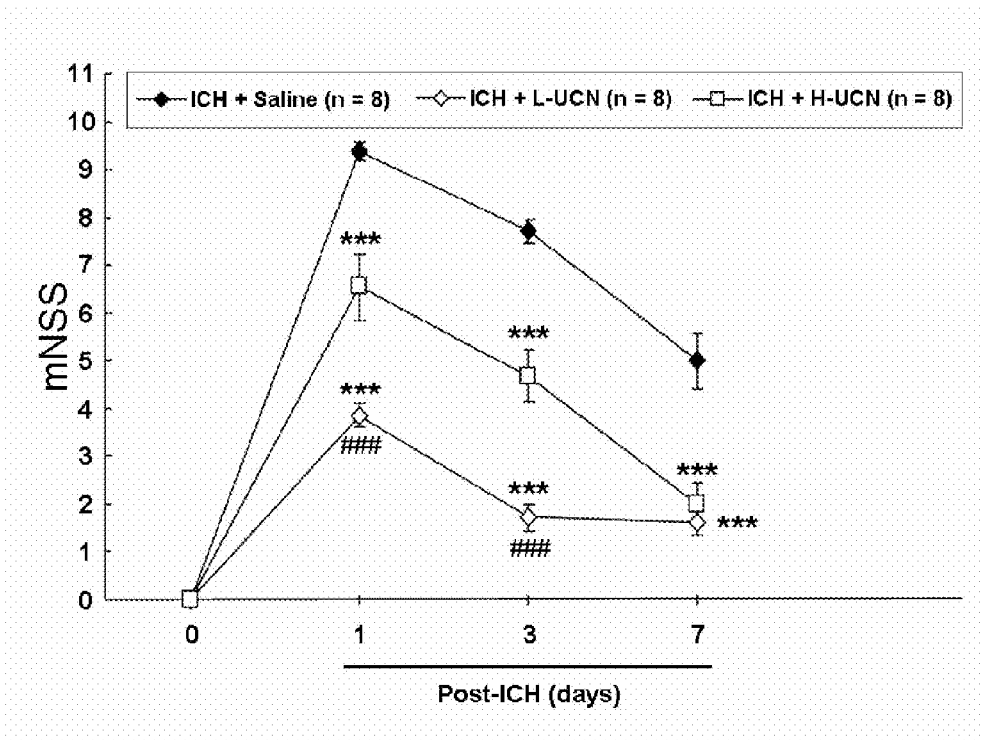
FIG. 2 shows reduction in ICH-induced neurological deficits by intraperitoneally post-treated UCN. (A) Collagenase model: Low- or High-UCN was administered at 60 minutes after ICH induced by intrastriatal injection of bacterial collagenase VII-S. (B) Blood infusion model: L-UCN was administered at 60 minutes after intrastriatal infusion of autologous blood. Values (means±SEMs) of modified neurological severity scores (mNSS) were examined on days 0, 1, 3, and 7 post-ICH. ICH, intracerebral hemorrhage; L-UCN, 2.5 µg/kg intraperitoneally; H-UCN, 25 µg/kg intraperitoneally. *$P<0.05$, $P<0.01$, *$P<0.001$ vs. ICH+Saline group; ##$P<0.01$, ###$P<0.001$ vs. ICH+H-UCN group.
Figure 2:
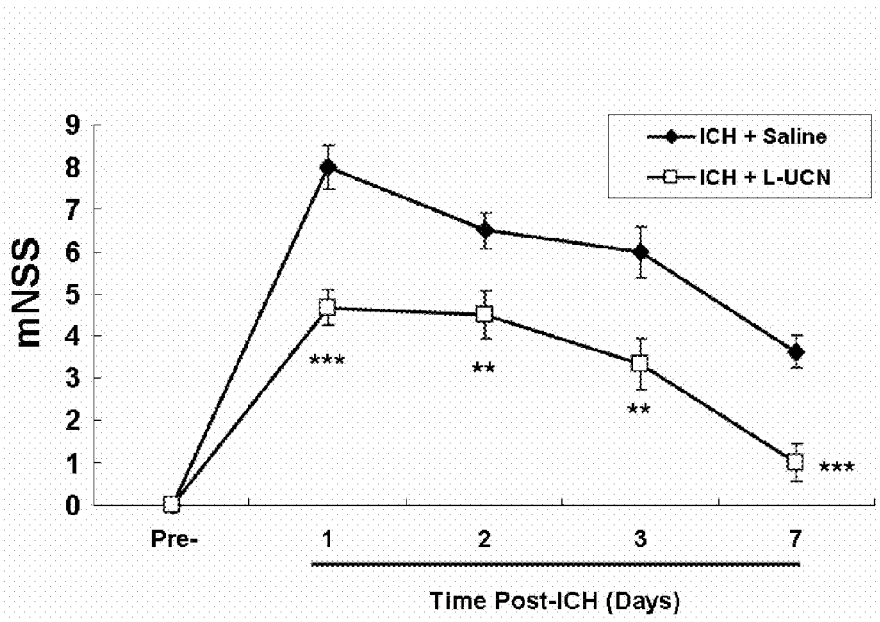

Dose-response effects of UCN (intracerebroventricular & intraperitoneal) and time course for the ICH-induced neurological deficits are shown in FIGS. 1 and 2. In all rats, the mNSS was 0 before the ICH, indicating a normal neurological function.

In the intracerebroventricular routes, the UCN administrations produced a dose-dependent reduction in the mNSS (an improvement from neurological deficits), most effectively at 5 μg, (p<0.001 vs. ICH+Saline group by repeated measures ANOVA followed by Tukey's post hoc test) (FIG. 1A). These data demonstrated that post-treatment with UCN significantly reduced the ICH-induced neurological deficits over 7 days. In autologous blood infusion models of ICH (FIG. 1B), the most effective dosage of UCN (5 μg) for the collagenase model was selected to investigate the therapeutic effect (FIG. 1B). Similar to the findings of the collagenase model, post-treatment with UCN resulted in a greater reduction in mNSS as compared with saline-post-treated rats [F (1, 36)=8.85 and p<0.05 by two-way ANOVA].

In the intraperitoneal routes, the ICH+Saline (control) group, the mNSS peaked up to 9.38±0.20 on day 1 and decreased time-dependently to 7.71±0.25 and 5.00±0.59 on days 3 and 7, respectively (FIG. 2A). In the ICH+L-UCN (2.5 μg/kg) group, the mNSS was reduced time-dependently from 3.86±0.70 on day 1 to 1.71±0.55, and thereafter declined to 1.63±0.46 on days 3 and 7, respectively; while in the ICH+H-UCN (25 μg/kg) group, the mNSS was reduced from 6.55±0.26 on day 1 to 4.68±0.29, and then declined to 2.00±0.26 on days 3 and 7, respectively. These results indicated that both L-UCN and H-UCN-significantly reduced neurological deficits on days 1, 3, and 7 (P<0.001 vs. ICH+Saline group) (FIG. 2A). However, the low dosage of UCN (2.5 μg/kg) showed greater reduction in the neurological deficits on days 1 and 3 (P<0.001 vs. ICH+H-UCN group). Similar to the findings of the collagenase model, post-treatment with UCN resulted in a greater reduction in mNSS as compared with ICH+Saline rats [F (1, 36)=8.85 and p<0.05 by two-way ANOVA] (FIG. 2B).

UCN has Hypotensive Effect Without Changing Other Physiological Parameters

Figure 3:
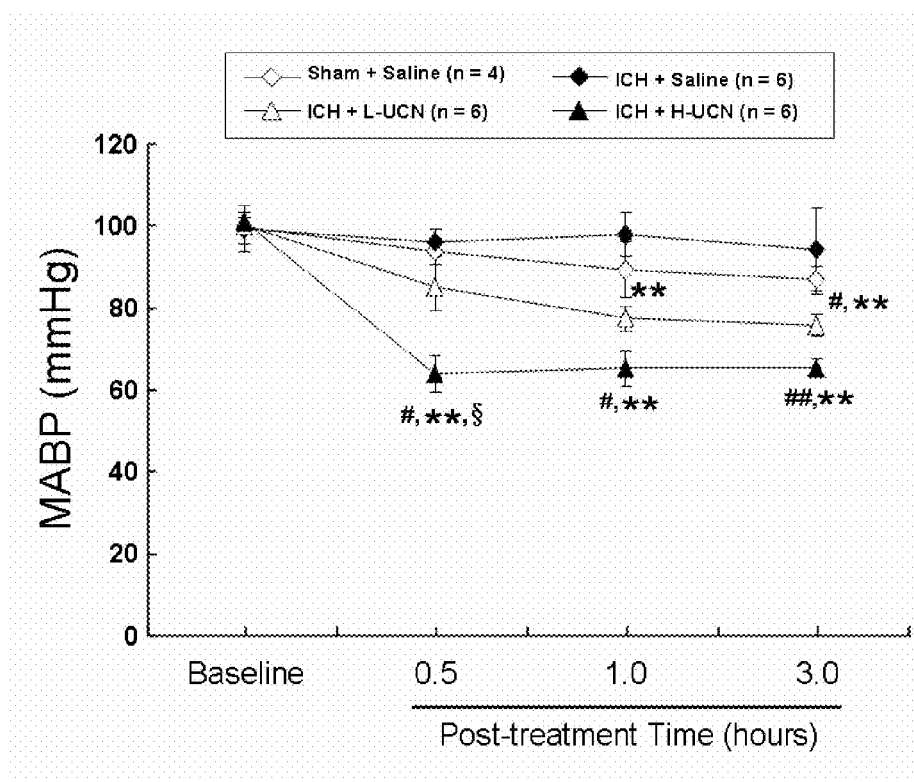
FIG. 3 shows cardiovascular effects of UCN. Mean arterial blood pressure (MABP) was measured up to 3 hours after treatments with low (L)- or high (H)-dose of UCN intraperitoneally in 4 groups of rats. Values are mean±SEM. *$P<0.05$, **$P<0.01$ in ICH +L-UCN or ICH+H-UCN groups vs. ICH+Saline group; #$P<0.05$, ###$P<0.001$ in ICH+L-UCN or ICH+H-UCN group vs. Sham+Saline group; §$P<0.05$ in ICH+H-UCN vs. ICH+L-UCN group. Data were analyzed repeated measures ANOVA followed by Bonferroni correction.
Figure 5:
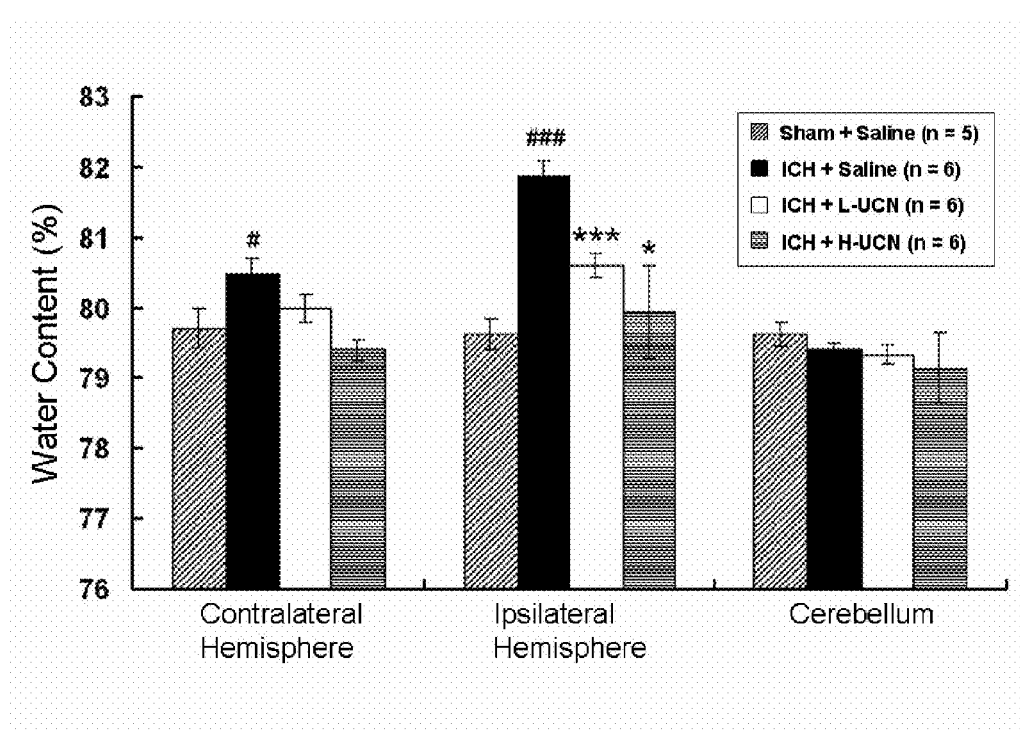
FIG. 5 shows reduction of brain water content by post-treatment with UCN intraperitoneally. Brain water content evaluated on day 3 post-ICH was expressed as a percentage of the wet weight: [(wet weight)−(dry weight)] (wet weight)−1×100%. Values are mean±SEM, calculated and analyzed by Student's t test. *$P<0.05$, ***$P<0.001$ vs. ICH+Saline group, #$P<0.05$, ###$P<0.001$ vs. Sham+Saline group.

There were no significant differences in baseline readings of mean arterial blood pressure (MABP), heart rate (HR), rectal temperature, pO$_2$, pCO$_2$ and pH among Sham+Saline, ICH+Saline and ICH+L-UCN (2.5 μg/kg, i.p.) groups, respectively (Table 1). One hour after ICH, intraperitoneally injection of UCN (2.5 μg/kg, i.p.) caused a significant decrease in MABP to a maximum of 25 mm Hg, and increase in HR maximally 35 beats/min started from 1.0 to 3.0 hours post-treatment time (FIG. 3), while a high dose of UCN (25 μg/kg, i.p.) decreased MABP to a maximum of 40 mm Hg, and increased HR maximally 45 beats/min started from 1.0 to 3.0 hours post-treatment time (FIG. 3). The rectal temperature, $pO_2$, $pCO_2$ and pH among groups for each of the time course were not significantly different (Table 1). There were no significant difference over 3 hours in mean arterial blood pressure after UCN administration (5 μg) intracerebroventricularly (FIG. 1C).

while that in the ICH+Saline group was increased to 80.48±0.23% (P<0.05); whereas those in the ICH+L-UCN and ICH+H-UCN were insignificantly reduced to 79.98±0.19% and 79.40±0.15%, respectively (FIG. 5). The water content of the ipsilateral hemisphere in the Sham+Saline group was 79.40±0.29%, while that in the ICH+Saline group was markedly increased to 81.88±0.20% (P<0.001) (FIG. 5). The water contents of the ipsilateral hemispheres in both ICH+L-UCN group and ICH+H-UCN group were significantly reduced to 80.60±0.17% (P<0.001) and 79.94±0.66% (P<0.05) (FIG. 5). No significant differences of water content were seen in the cerebellum among groups.

TABLE 1

Comparisons of physiological parameters in Sham + Saline, ICH + Saline, and ICH + L-UCN (2.5 μg/kg, i.p.) groups

| | Post-treatment Time (hours) | | | |
|---|---|---|---|---|
| RT (° C.) | Baseline | 0.5 | 1.0 | 3.0 |
| Sham + Saline (n = 4) | 37.20 ± 0.11 | 37.05 ± 0.16 | 37.10 ± 0.09 | 37.00 ± 0.09 |
| ICH + Saline (n = 6) | 36.92 ± 0.08 | 36.88 ± 0.06 | 36.93 ± 0.03 | 35.63 ± 0.81 |
| ICH + L-UCN (n = 6) | 36.92 ± 0.05 | 36.95 ± 0.03 | 37.00 ± 0.05 | 36.97 ± 0.02 |
| $pO_2$ (mmHg) | Baseline | 0.5 | 1.0 | 3.0 |
| Sham + Saline (n = 4) | 92.50 ± 1.26 | 93.63 ± 3.79 | 95.18 ± 6.30 | 102.68 ± 4.76 |
| ICH + Saline (n = 6) | 95.73 ± 4.16 | 104.00 ± 5.93 | 104.77 ± 4.79 | 126.27 ± 12.11 |
| ICH + L-UCN n = 6) | 100.00 ± 4.40 | 105.24 ± 6.00 | 107.28 ± 5.35 | 107.90 ± 5.59 |
| $pCO_2$ (mmHg) | Baseline | 0.5 | 1.0 | 3.0 |
| Sham + Saline (n = 4) | 50.80 ± 1.44 | 50.13 ± 1.72 | 45.25 ± 0.57 | 44.43 ± 1.82 |
| ICH + Saline (n = 6) | 49.67 ± 1.54 | 45.04 ± 1.44 | 46.18 ± 1.89 | 36.20 ± 5.14 |
| ICH + L-UCN (n = 6) | 46.73 ± 1.80 | 45.07 ± 1.05 | 42.60 ± 2.44 | 43.25 ± 1.59 |
| pH | Baseline | 0.5 | 1.0 | 3.0 |
| Sham + Saline (n = 4) | 7.39 ± 0.01 | 7.40 ± 0.01 | 7.41 ± 0.01 | 7.42 ± 0.01 |
| ICH + Saline (n = 6) | 7.39 ± 0.01 | 7.40 ± 0.01 | 7.40 ± 0.01 | 7.39 ± 0.02 |
| ICH + L-UCN (n = 6) | 7.37 ± 0.02 | 7.39 ± 0.01 | 7.42 ± 0.01 | 7.42 ± 0.01 |

Values are given as mean ± SEM.
ICH, intracerebral hemmorrage;
L-UCN, low dose urocortin,
i.p., intraperitoneally;
RT, rectal temperature.

UCN Reduces Brain Edema

Figure 4:
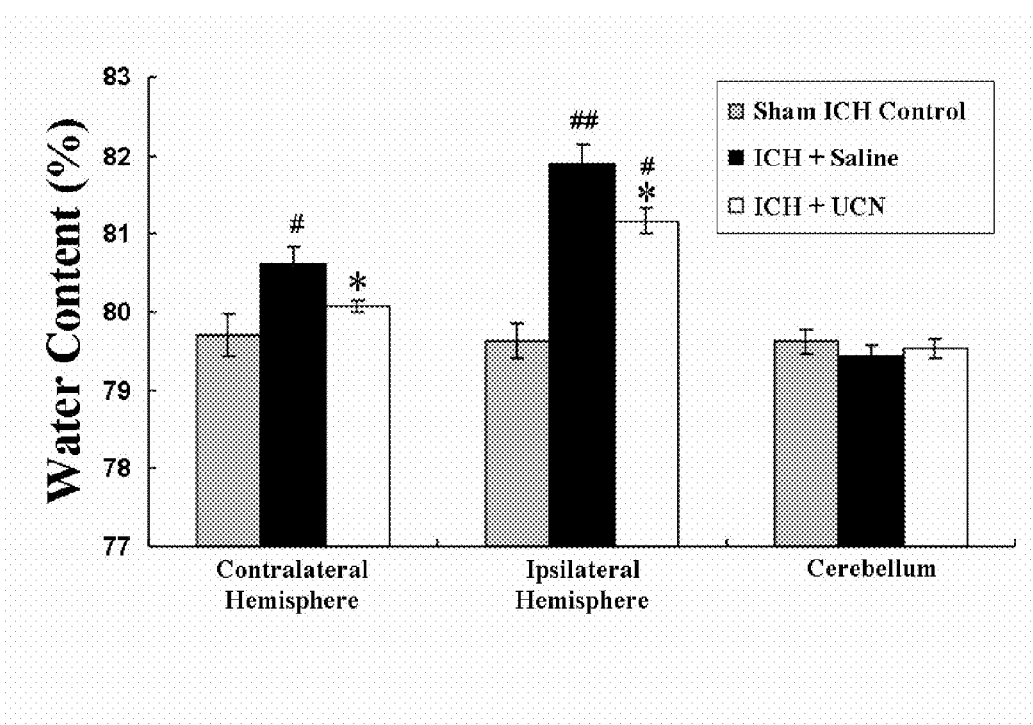
FIG. 4 shows effects of intracerebroventricular administration of UCN on brain water content on day 3 after collagenase-induced ICH. The water content was significantly increased in contralateral (#$P<0.05$) and ipsilateral (##$P<0.01$) hemispheres of the ICH+Saline group (n=6) as compared with the Sham ICH Control (n=4). These increases were significantly reduced (*$P<0.05$ for the contralateral and the ipsilateral) in the ICH+UCN group (post-treatment with UCN, 5 μg, i.c.v., n=6). Note that the reduced water content in the ipsilateral hemisphere (#$P<0.05$) of the ICH+UCN groups was still greater than that in the Sham ICH Control. The water content in the cerebellum appeared to be not changed in all groups. Data represent means±SEM analyzed by Student's t test.

Intracerebroventricular Experiment:

On day 3 post-ICH, brain water contents of contralateral and ipsilateral hemispheres in the Sham ICH Control (n=4) were 79.63±0.22% and 79.70±0.28% (p>0.05), respectively (FIG. 4). In the ICH+Saline group, the water content of the contralateral hemisphere was increased to 80.63±0.21% (p<0.05), and that of the ipsilateral hemisphere to 81.89±0.24% (p<0.01). In the ICH+UCN group, however, brain water content of the contralateral hemisphere was reduced to 80.08±0.08% (p<0.05) and that of the ipsilateral hemisphere to 81.16±0.16% (p<0.05). Note that the reduced water content in the ipsilateral hemisphere (p<0.05) of the ICH+UCN groups was still greater than that in the Sham ICH Control. The brain water content of the cerebellum was essentially not affected among these three groups (n=6 each group). These findings indicated that unilateral ICH produced cerebral edema on both contra- and ipsilateral hemispheres, but greater on the ipsilateral side; and that unilateral UCN post-treatment significantly reduced the cerebral edema in both contra- and ipsilateral hemispheres.

Intraperitoneal Experiment:

On day 3 post-ICH, water content of the contralateral hemisphere in the Sham+Saline group was 79.45±0.34%, These findings indicate that UCN post-treatment significantly reduces the ICH-induced cerebral edema. The reduction of brain edema by H-UCN was not significantly different from that by L-UCN (FIG. 5).

Penetration of UCN Through the BBB into Striatum

Figure 6:
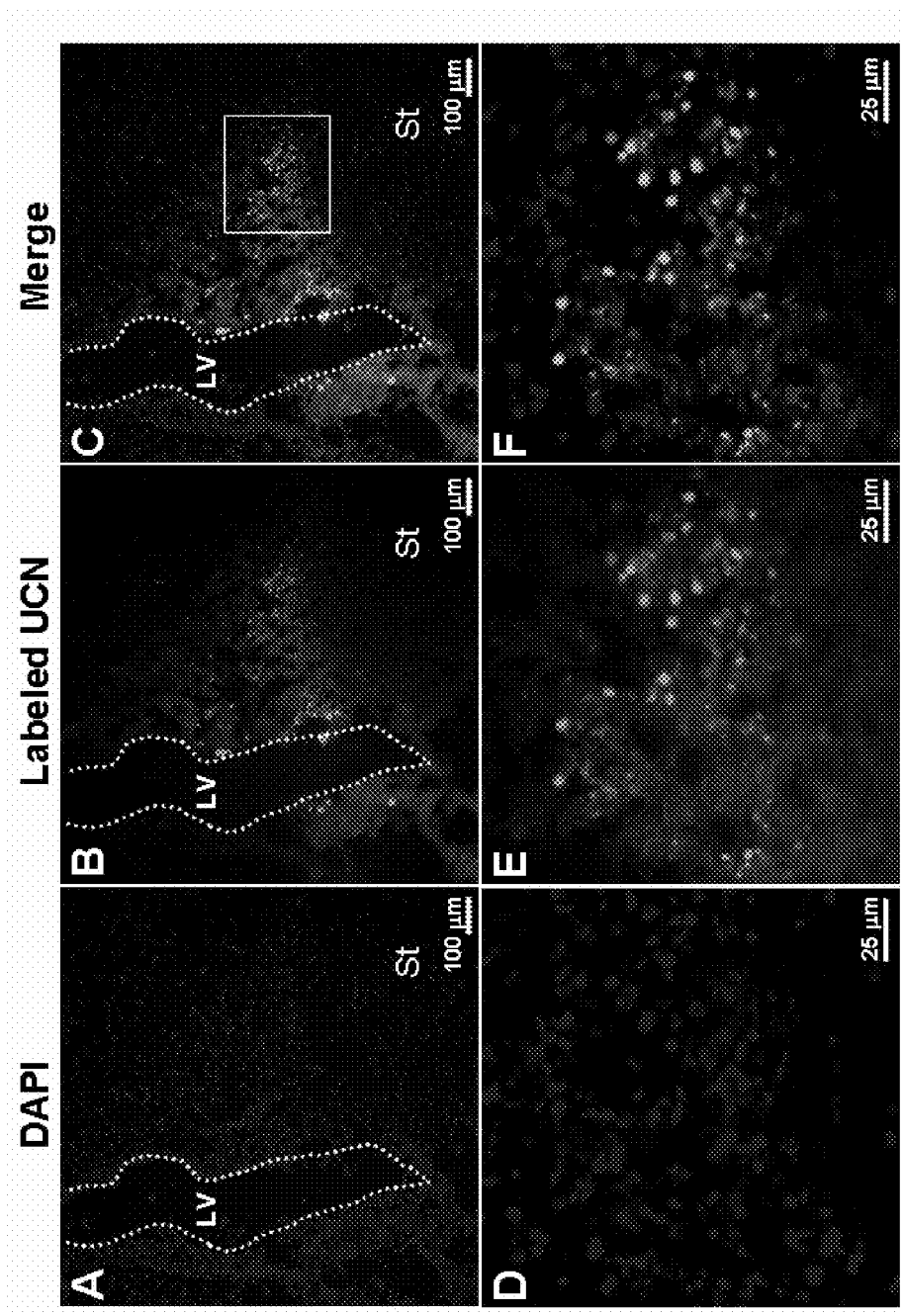
FIG. 6 shows striatal histological sections stained with DAPI and fluorescence-labeled UCN. UCN labeled with Alex Fluor 488 dye was injected into lateral ventricle (LV) one hour after collagenase-ICH. At three hours after the labelled-UCN injection, DAPI (A and D, blue) and fluorescence-labeled UCN (B and E, green) were detected by fluorescent microscopy in injured striatum (St). Both DAPI and labeled UCN were co-localized in cell nuclei (C and F, merge).
Figure 7:
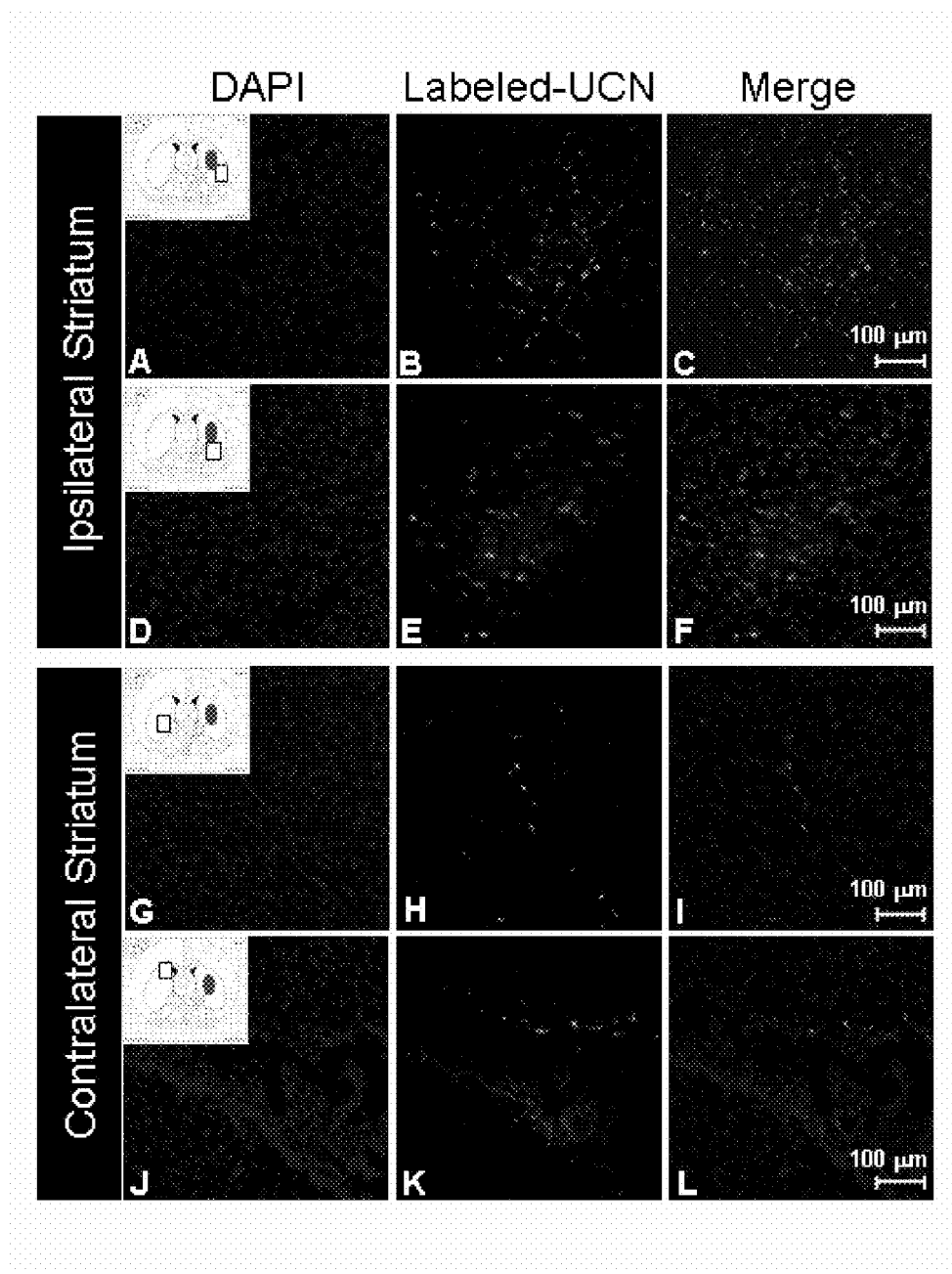
FIG. 7 shows striatal histological sections stained with DAPI and fluorescence-labeled UCN for evaluation of UCN penetration into the striatum. UCN labeled with Alex Fluor 488 dye was injected intraperitoneally one hour after unilateral collagenase-ICH. At three hours after the labelled-UCN injection, DAPI (A, D, G & J, blue) and fluorescence-labeled UCN (B, E, H, & J, green) were detected by fluorescent microscopy in ipsilateral and contralateral striatum.

To examine whether UCN can penetrate into striatal parenchyma to exert its function, Alexa Fluor® 488 labeled-UCN was administrated intracerebroventricular (FIG. 6) and intraperitoneally (FIG. 7) one hour after ICH. To test whether UCN can penetrate from cerebral ventricle into striatal parenchyma, it was demonstrated that after injection of the fluorescence labeled-UCN into one side of the lateral ventricle (LV) of the collagenase-ICH rat, both DAPI and fluorescence-labeled UCN were co-localized in cell nuclei of the striatum on the ipsilateral (FIGS. 6C and 6F) but not on the contralateral side (data not shown). These results indicate that the UCN can diffuse from the lateral ventricle into the cell nucleus of the same side striatum. Besides, three hours after intraperitoneal injection of fluorescence-labeled UCN (2.5 μg/kg), the labeled UCN was localized in both ipsilateral (FIGS. 7A to 7F) and contralateral side (FIGS. 7G to 7L) of the striatum. It appeared to be more prominent on the ipsilateral side. These results indicate that the UCN administered via clinically amenable routes comprising, but not limited to, injections via intraperitoneal, intravenous, intramuscular, or subcutaneous routes, can diffuse from the systemic circulation into the damaged striatum or other brain parts.

UCN Reduces Lesion Volume but Not Hemorrhagic Volume

The content of hemoglobin determined by spectrophotometric measurement can be a good indication of the hemorrhagic volume.

Figure 8:
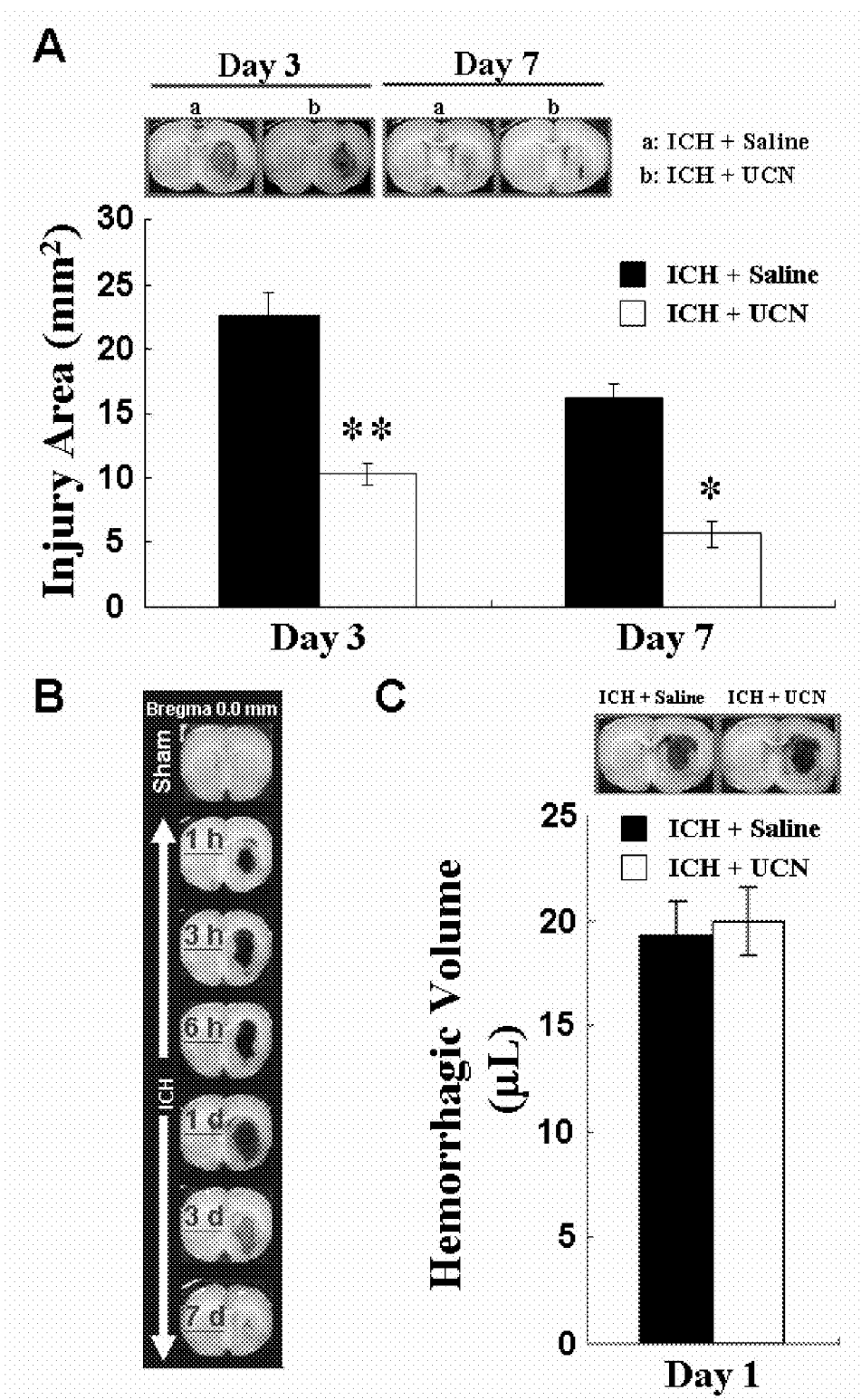
FIG. 8 shows effect of intracerebroventricular administration of UCN on injured area on day 3 and 7 after ICH. (A) Photographs of representative brain sections show changes of the injured areas in the ICH+Saline and the ICH+UCN (5 μg, i.c.v.) on days 3 and 7. Histograms show that the ICH+UCN (5 μg, i.c.v.) significantly reduced the injured area on day 3 (**$P<0.01$, n=6) and day 7 (*$P<0.05$, n=6) as compared to the ICH+Saline on day 3 (n=6) and day 7 (n=6), respectively. (B) Brain sections show sizes of hemorrhagic areas in a Sham ICH rat and 6 ICH rats killed at post 1, 3, 6 hours, or 1, 3, and 7 days. (C) The accumulated hemorrhagic volume determined at 24 hours post-ICH was not significantly different between ICH+UCN and ICH+Saline groups (n=5 each group).

Intracerebroventricular Experiment:

Post-treatment with UCN (the ICH+UCN group) significantly reduced injured area on day 3 from $22.62\pm1.79$ mm$^2$ to $16.14\pm1.22$ mm$^2$ ($p<0.01$, $n=5$) and on day 7 from $10.27\pm0.86$ mm$^2$ to $5.62\pm1.04$ mm$^2$ ($p<0.05$, $n=5$) after ICH insult (FIG. 8A). Changes in hemorrhagic areas in a Sham ICH Control rat and 6 ICH rats killed at post 1, 3, 6 hours, or 1, 3, and 7 days were shown in FIG. 8B. The hemorrhagic area developed to the maximum at 24 hours (1 day). The sizes of hemorrhagic area were equal for the ICH+Saline and the ICH+UCN ($n=1$ each) as shown in FIG. 8C (upper). Therefore, the accumulated hemorrhagic volume was determined at 24 hour post ICH. It is demonstrated that the accumulated hemorrhagic volume was not significantly different between ICH+UCN and ICH+saline groups ($p>0.05$, $n=5$ each group).

Figure 9:
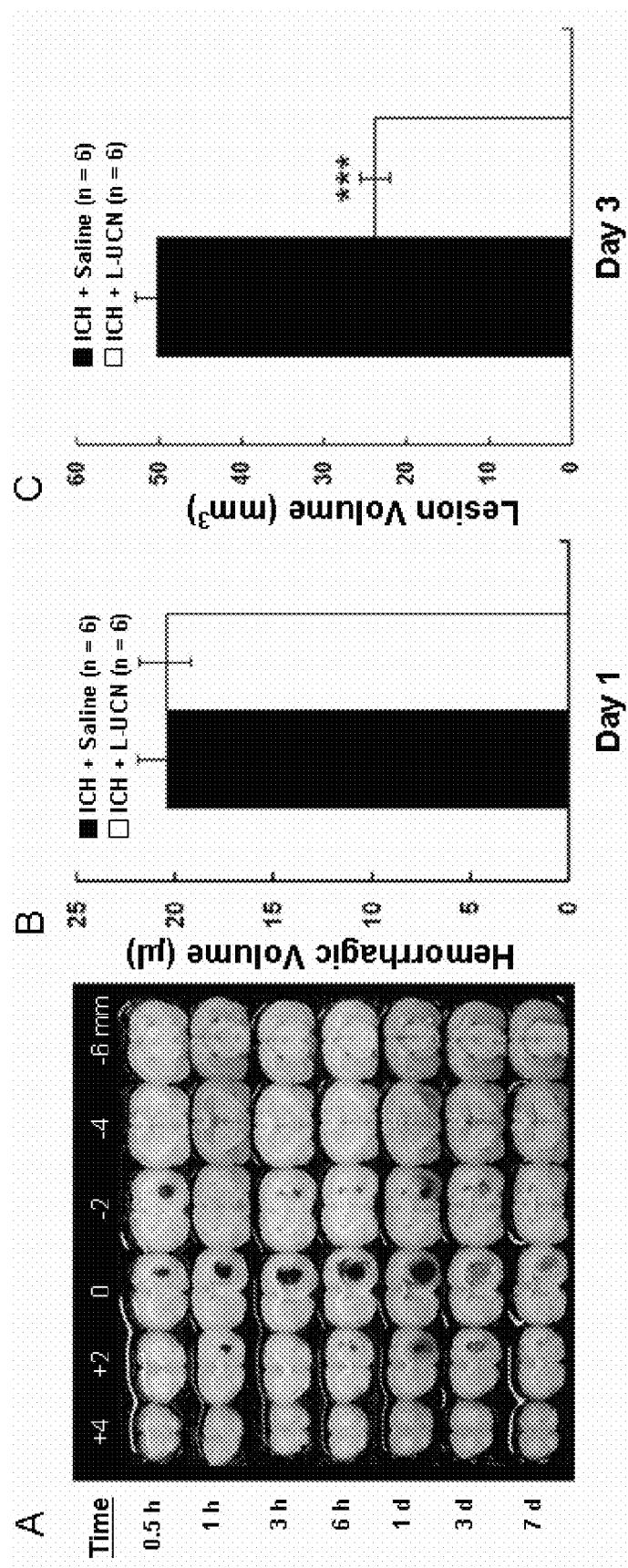
FIG. 9 shows post-treatment with UCN intraperitoneally does not affect hemorrhagic volume but reduces lesion volume. (A) Representative coronal sections (2 mm thickness) show brain hemorrhagic areas of seven rats killed on 0.5, 1, 3, 6 h (hours), 1, 3, 7 d (days) after ICH. (B) Hemorrhagic volume on day 1 post ICH was determined by spectrophotometric assay. (C) Lesion volume on day 3 post ICH was determined by morphometric measurement. Values are means±SEMs. ***$P<0.001$ vs. ICH+Saline group.

Intraperitoneal Experiment:

FIG. 9A shows the hemorrhagic volume peaked on day 1 post-ICH. The hemorrhagic volume on day 1 post-ICH was not significantly different between the ICH+Saline and ICH+L-UCN groups (FIG. 9B), indicating UCN did not affect bleeding (hemorrhagic volume). As the hemorrhagic volume was not important at the time longer than 1 day post-ICH, a lesion volume by morphometric measurement was used for the day 3 post-ICH instead. The lesion volume refers to the volume of residual blood clot and damaged tissue. It was significantly reduced in ICH+L-UCN as compared with ICH+Saline group ($23.73\pm1.79$ mm$^3$ vs. $50.26\pm2.67$ mm$^3$, $P<0.001$) (FIG. 9C), suggesting that UCN can reduce hematoma volume or lesion size.

UCN Attenuates BBB Disruption

Since BBB disruption is very likely a contributory cause of brain edema that peaks on day 3 post-ICH, changes in BBB disruption was determined by Evans blue on the same day.

Figure 10:
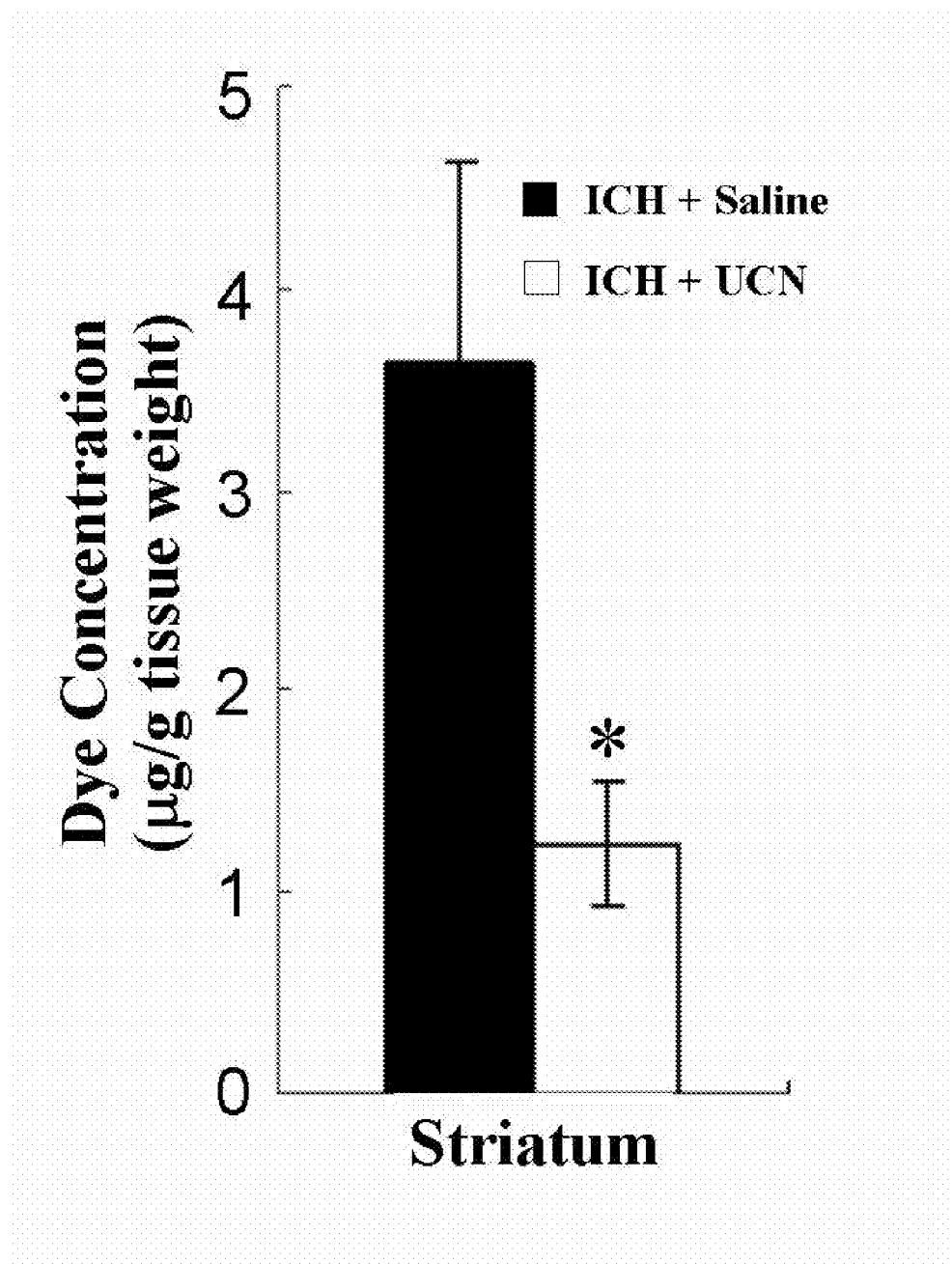
FIG. 10 shows quantitative analysis of Evans Blue dye concentration in striatum sections on day 3 after the collagenase-induced ICH. Post-treatment with UCN intracerebroventricular (ICH+UCN, 5 μg, n=6) significantly reduced the BBB leakage within ipsilateral striatum (*$P<0.05$) as compared with the vehicle control (ICH+Saline, n=6).

Intracerebroventricular Experiment:

On day 3 after the ICH, Evans blue concentrations of the hemorrhagic (ipsilateral) striatum in the ICH+Saline and ICH+UCN groups were $3.63\pm0.99$ µg/g and $1.24\pm0.31$ µg/g ($p<0.05$, $n=6$ for each group), respectively (FIG. 10). The results indicated that post-treatment with UCN significantly reduced the ICH-induced BBB leakage. The dye concentrations of the contralateral striatum, contralateral and ipsilateral cortices, and cerebellum were not different between the ICH+Saline and ICH+UCN groups, indicating that the unilateral striatal ICH in the present experimental condition appeared not to affect the BBB of the contralateral striatum, contra- and ipsi-lateral cerebral cortices as well as the cerebellum.

Figure 11:
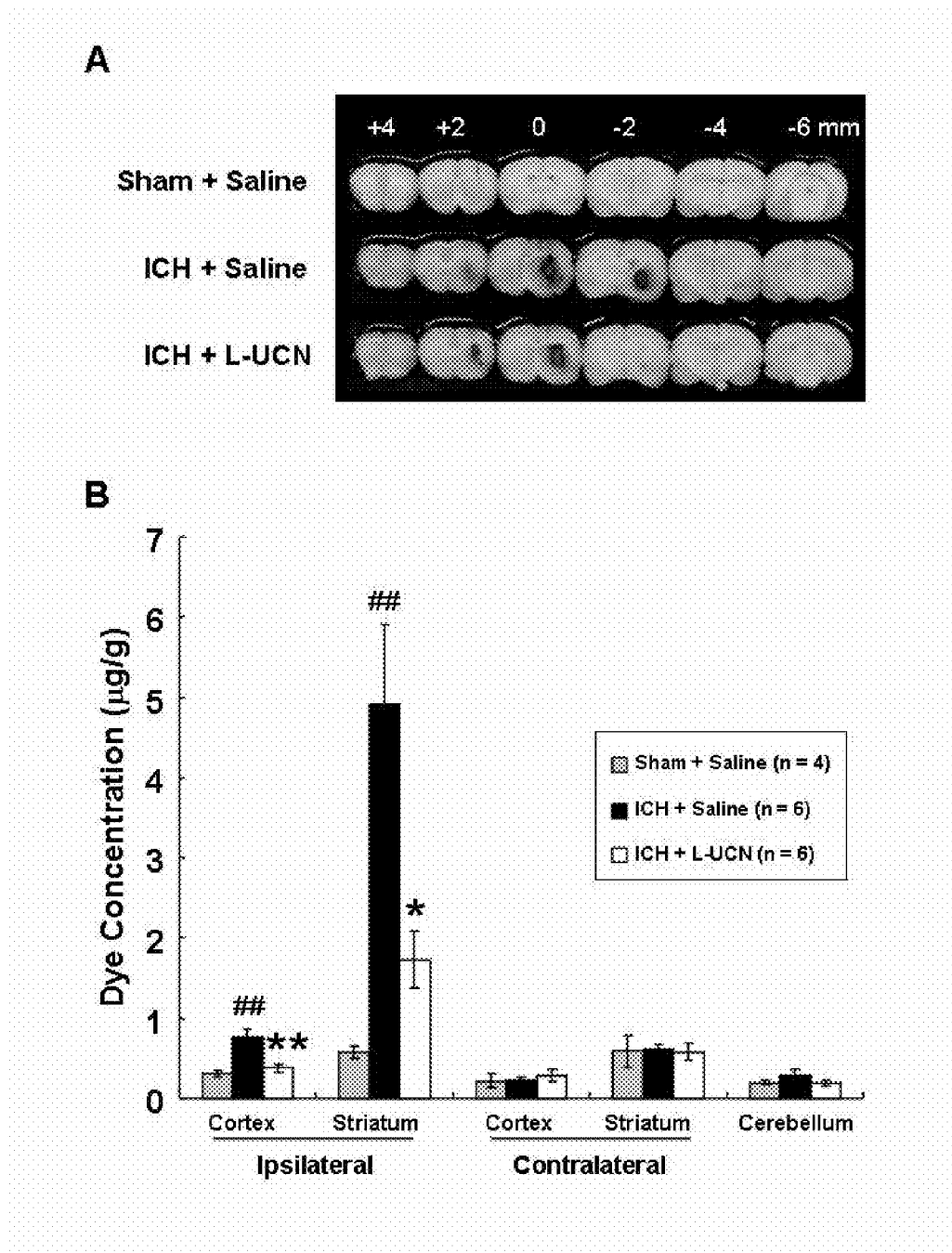
FIG. 11 shows reduction in BBB disruption in ipsilateral cortex and striatum by post-treatment with UCN intraperitoneally. (A) Representative brain coronal sections (2 mm thickness) show Evans blue extravasation on day 3 post-ICH. Collagenase was injected at 0.0 mm posterior, 3.0 mm right, 5.0 mm ventral to bregma skull surface. (B) Comparisons of dye concentrations of various brain tissues among Sham+Saline, ICH+Saline, and ICH+L-UCN (2.5 μg/kg, i.p.) groups. The dye concentration was expressed as mg/g of tissue weight and calculated from a standard curve obtained from known amounts of the dye. Values are mean±SEM. *$P<0.05$, $P<0.01$, *$P<0.001$ vs. ICH+Saline group, #$P<0.05$, ##$P<0.01$ vs. Sham+Saline group.

Intraperitoneal Experiment:

Representative brain coronal sections (FIG. 11A) show Evans blue extravasation on day 3 post-ICH was markedly reduced in the ICH+L-UCN group compared with the ICH+Saline. Dye concentration of the ipsilateral cortex and striatum in the ICH+Saline group was significantly greater than that of Sham +Saline group ($0.77\pm0.09$ µg/g vs. $0.31\pm0.04$ µg/g, $P<0.01$; and $4.92\pm0.99$ µg/g vs. $0.57\pm0.08$ µg/g, $P<0.01$, respectively), indicating ICH caused BBB disruption of the ipsilateral cortex and striatum (FIG. 11B). The ICH+L-UCN group exhibited a significantly lower dye concentration than the ICH+Saline group in the ipsilateral cortex ($0.38\pm0.05$ µg/g vs. $0.77\pm0.09$ µg/g, $P<0.01$) and the striatum ($1.73\pm0.36$ µg/g vs. $4.92\pm0.99$ µg/g, $P<0.05$), indicating that UCN significantly reduced the ICH-induced BBB disruption. Evans blue dye concentrations in other tissues, namely cerebellum, and contralateral cerebral cortex and striatum, appeared to be not changed in all three groups (FIG. 11B).

UCN Reduces Pro-inflammatory Cytokine Levels in Striatal Tissue

Figure 12:
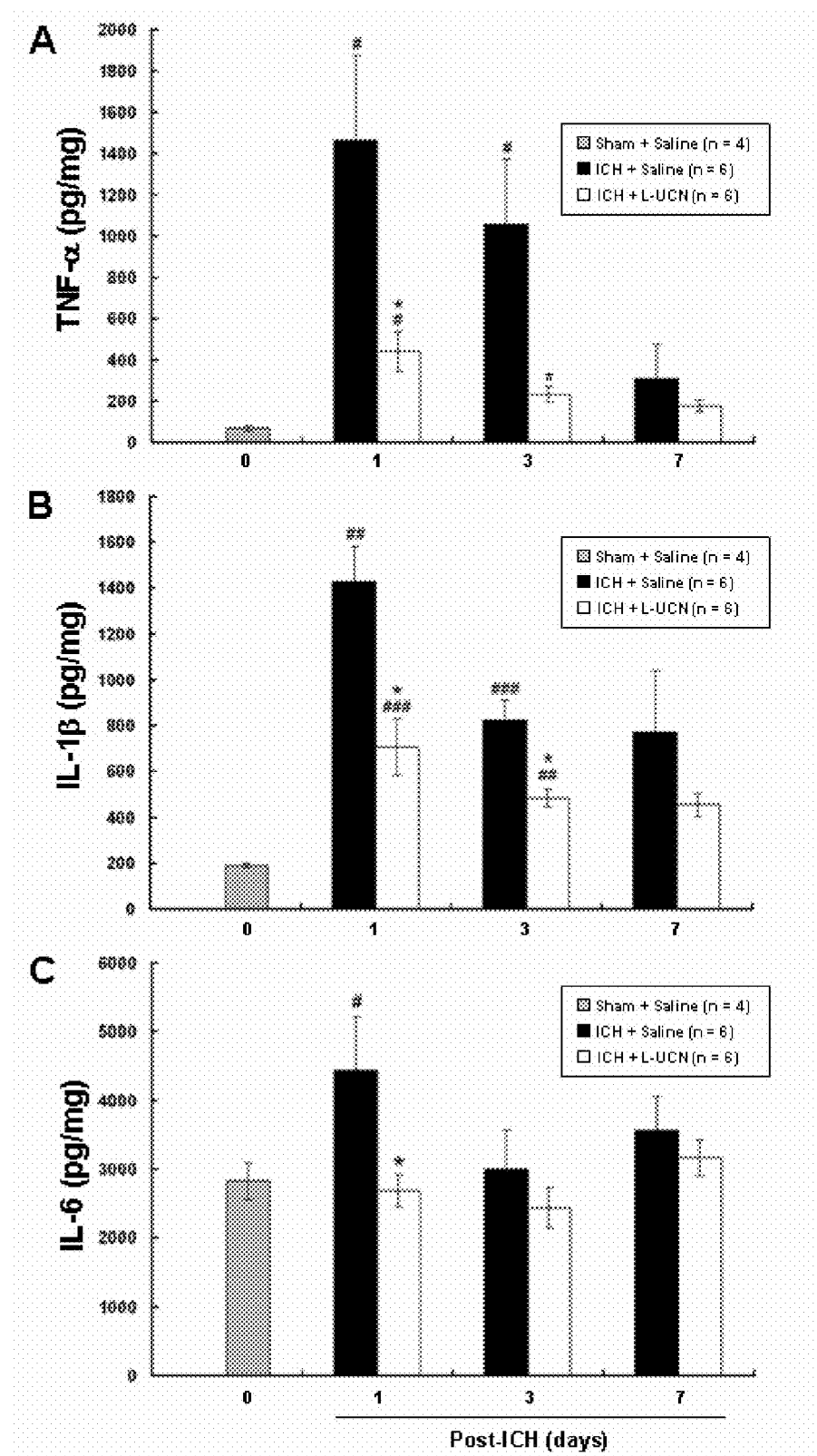
FIG. 12 shows striatal tissue levels of TNF-α (A), IL-1β (B) and IL-6 (C) in Sham+Saline group, ICH+Saline group, ICH+L-UCN (2.5 μg/kg, i.p.) group. Values are mean±SEM. *$P<0.05$, $P<0.01$, *$P<0.001$ vs. ICH+Saline group, #$P<0.05$, ##$P<0.01$, ###$P<0.001$ vs. Sham+Saline group.

Pro-inflammatory cytokine (TNF-α, IL-1β, and IL-6) levels of the ipsilateral striatum in the ICH+Saline group were significantly increased on day 1 post-ICH as compared with day 0 pre-ICH of the Sham +Saline group; however, levels of TNF-α (FIG. 12A) and IL-1β (FIG. 12B) maintained high, albeit getting lower, throughout days 3 and 7. These high levels of cytokines were significantly reduced in the ICH+L-UCN group throughout days 1, 3, and 7 post-ICH, but did not return to the control (normal) level in these days. The level of IL-6 (FIG. 12C) in the ICH+Saline group was also increased on day 1 post-ICH as compared with pre-ICH (day 0) level in the Sham+Saline group; while this increase was also reduced in the ICH+L-UCN group on day 1 post-ICH. The level of IL-6, however, returned to the control level without UCN treatment on days 3 and 7 post-ICH.

UCN Reduces Microglial Activation and Neuron Loss

Figure 13:
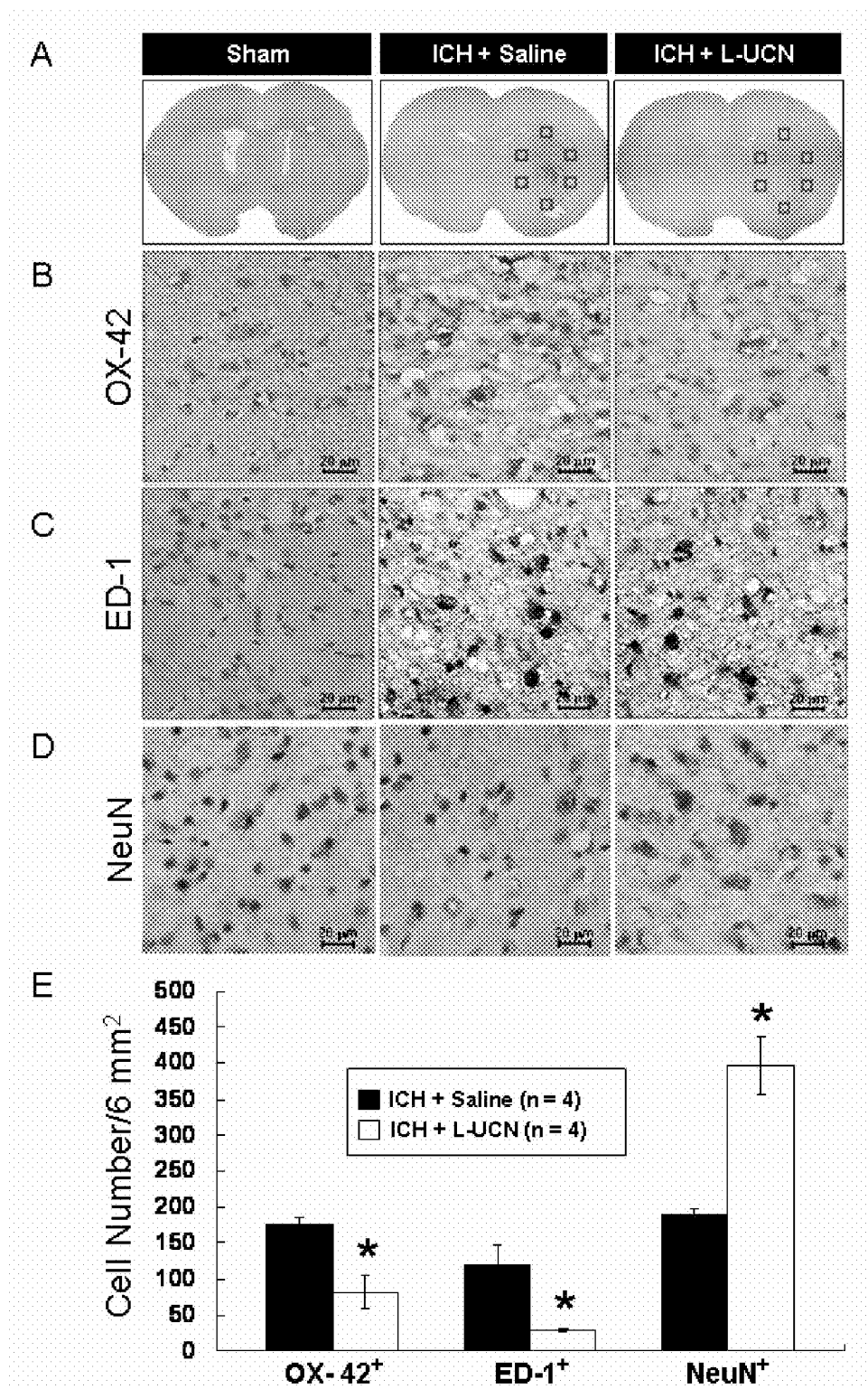
FIG. 13 shows immunohistochemistry analysis of microglial activation and neuronal loss on day 3 post-treatment with UCN intraperitoneally. Representative photomicrographs show: (A) low power images of peri-hematomal regions as indicated by squares; (B) high power images stained with Ox-42; (C) ED-1; and (D) NeuN, in Sham+Saline, ICH+Saline, and ICH+L-UCN groups. (E) Numbers of positively stained cells (OX 42$^+$, ED-1$^+$, and NeuN$^+$) in 6 squares (totally 6 mm$^2$) were plotted for the ICH+Saline group and the ICH+Low-UCN groups. Values are mean±SEM. *$P<0.05$ vs. ICH+Saline group. Bar=20 μm.

Compared to the ICH+Saline group (FIG. 13E), when examined on day 3 post-ICH, the ICH+L-UCN group had significantly lower number of OX-42$^+$ microglial cells ($82.00\pm22.86$ cells/6 mm$^2$ vs. $175.33\pm10.87$ cells/6 mm$^2$, $P<0.05$, FIG. 13B), of ED-1$^+$ cells ($28.50\pm2.65$ cells/6 mm$^2$ vs. $118.00\pm28.72$ cells/6 mm$^2$, $P<0.05$, FIG. 13C), and NeuN$^+$ cells loss ($397.00\pm39.74$ cells/6 mm$^2$ vs. $189.25\pm8.22$ cells/6 mm$^2$, $P<0.05$, FIG. 13D).

Choose of Dosage and Administering Route for Urocortin

The dosages of intracerebroventricular injection of UCN were obtained from empirical trials, because there is no available investigation on the therapeutic dosage of UCN for ICH treatment. The high dose (25 µg/kg body weight) of UCN by intraperitoneal route caused lesser effectiveness than the low dose (2.5 or 25 µg/kg body weight) of UCN in attenuating neurological deficits. A plausible explanation might be due to a potent hypotensive action of urocortin. A high dose (25 µg/kg body weight) of UCN in a bolus intraperitoneal injection induced a marked fall in mean arterial blood pressure (MABP) by 40-50 mmHg, leading to a significant reduction of the cerebral blood flow (CBF) by 25%, while a bolus intravenous injection of the same dose even induced a much more abrupt fall of MABP, leading to a more reduction of CBF by 40-45%. Therefore, the severe hypotensive effect of urocortin should be avoided to prevent further damage to the already damaged tissues. A safety way of urocortin administration thus is demonstrated as using a bolus intraperitoneal administration of low and moderate dosages (2.5 or less than 25 µg/kg body weight) of UCN, or alternatively a slowly intravenous infusion of these dosage ranges.

What is claimed is:

1. A method for treating brain injury in a subject, comprising administering an effective amount of urocortin to the subject in need thereof, wherein the brain injury is stroke, intracerebral hemorrhage, or a combination thereof.

2. The method of claim 1, wherein the urocortin is administered to the subject by one of intracerebroventricular injection, intraperitoneal injection, intravenous bolus administration, or any combination thereof.

3. The method of claim 2, wherein the urocortin is delivered intracerebroventricularly to the subject at an amount of about 0.05 to about 5 µg/kg per subject.

4. The method of claim 2, wherein the urocortin is delivered intraperitoneally to the subject at an amount of about 0.5 to about 25 µg/kg per subject.

5. The method of claim 4, wherein the urocortin is delivered intraperitoneally to the subject at an amount of about 1 to about 4 µg/kg per subject.

6. The method of claim 2, wherein the urocortin is delivered intravenously to the subject in the form of a bolus.

7. The method of claim 6, wherein the urocortin is delivered intravenously to the subject at an amount of about 2.5 to about 25 µg/kg per subject.

8. The method of claim 1, wherein the urocortin is one of naturally occurring human urocortin, naturally occurring non-human urocortin, or non-naturally occurring urocortin.

9. The method of claim 1, wherein the treatment of brain injury comprises suppression of microglial activation.

10. The method of claim 1, wherein the treatment of brain injury comprises suppression of inflammatory cytokine production.

11. The method of claim 1, wherein the treatment of brain injury comprises suppression of brain edema.

12. The method of claim 1, wherein the treatment of brain injury comprises suppression of blood-brain barrier damage.

13. The method of claim 1, wherein the subject is a mammal.

14. The method of claim 1, wherein the subject is human.

* * * * *